United States Patent
Stearns

(10) Patent No.: US 11,850,178 B1
(45) Date of Patent: Dec. 26, 2023

(54) EPICONDYLITIS SUPPORT

(71) Applicant: Jeffrey Brian Stearns, Hopatcong, NJ (US)

(72) Inventor: Jeffrey Brian Stearns, Hopatcong, NJ (US)

(73) Assignee: BULLSEYE BRACE, INC.

( * ) Notice: Subject to any disclaimer, the term of this patent is extended or adjusted under 35 U.S.C. 154(b) by 146 days.

(21) Appl. No.: 17/342,333

(22) Filed: Jun. 8, 2021

Related U.S. Application Data

(60) Provisional application No. 63/039,920, filed on Jun. 16, 2020.

(51) Int. Cl.
*A61F 5/01* (2006.01)
*A61F 5/32* (2006.01)

(52) U.S. Cl.
CPC .............. *A61F 5/013* (2013.01); *A61F 5/32* (2013.01)

(58) Field of Classification Search
CPC .. A61F 5/01; A61F 5/0106; A61F 5/30; A61F 5/40; A61F 5/013; A61F 5/13; A61F 5/32; A61F 5/0118; A61F 5/0125; A61F 5/05841; A61F 5/05858; A61F 2013/0028; A61F 13/023; A61F 13/0283; A61F 13/025; A61F 13/0246; A61F 13/0259; A61F 13/061; A61F 13/064; A61F 13/108; A41D 13/0568; B32B 5/18; C09J 7/21; C09J 7/38; A61L 15/425; A61L 15/58
USPC .......................... 602/54, 58, 59, 76; 128/845
See application file for complete search history.

(56) References Cited

U.S. PATENT DOCUMENTS

| | | | | |
|---|---|---|---|---|
| 2,740,403 | A * | 4/1956 | Berthol | A61F 13/0223 602/44 |
| 4,479,495 | A * | 10/1984 | Isaacson | A61H 39/04 D24/211 |
| 5,063,913 | A * | 11/1991 | Nyi | A61F 13/107 602/20 |
| 6,702,772 | B1 | 3/2004 | Colditz | |
| 2002/0173738 | A1* | 11/2002 | Rogalski | A61F 13/108 602/20 |
| 2004/0210178 | A1* | 10/2004 | Weaver, II | A61F 13/108 602/61 |
| 2007/0021706 | A1* | 1/2007 | Braunstein | A61F 5/0109 602/62 |
| 2008/0188788 | A1* | 8/2008 | Serola | A61F 5/02 602/75 |

(Continued)

*Primary Examiner* — Ophelia A Hawthorne
*Assistant Examiner* — Michael Milo
(74) *Attorney, Agent, or Firm* — QuickPatents, Inc.; Kevin Prince

(57) ABSTRACT

A supportive brace to be worn circumferentially around the forearm for preventing and reducing pain and discomfort associated with epicondylitis (Tennis Elbow or Golfer's Elbow) of the elbow is disclosed. The brace includes a padded counterforce strap assembly band circumferentially fitted around the forearm. The strap assembly has an elastomeric buttress positioned to apply targeted compression to the ECRB. A toric ring forms a cushioned border around the concavity on the dorsal face of the elastomeric buttress, so that when the band is fittingly secured around the forearm about 1-1.5 in distal to either of the epicondyles, the hemispherical/ovaloid convex shape on the inside face of the elastomeric buttress exerts controlled pressure to tissues associated with the epicondylitis.

9 Claims, 6 Drawing Sheets

(56) References Cited

U.S. PATENT DOCUMENTS

2014/0114219 A1* 4/2014 Nazari ................. A61B 90/02
                                                        601/84
2019/0388263 A1* 12/2019 Emslander ............ A61L 15/125

* cited by examiner

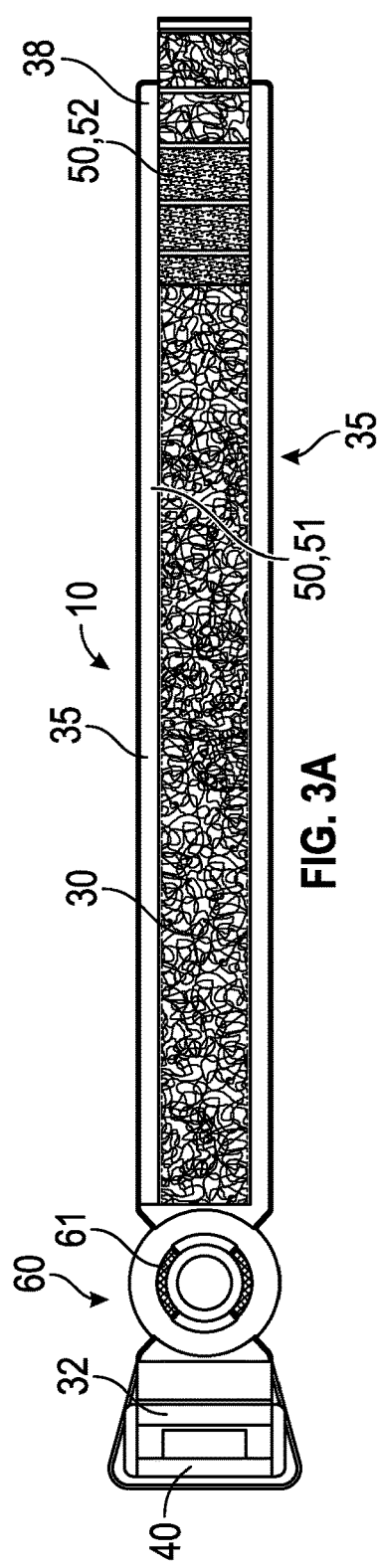
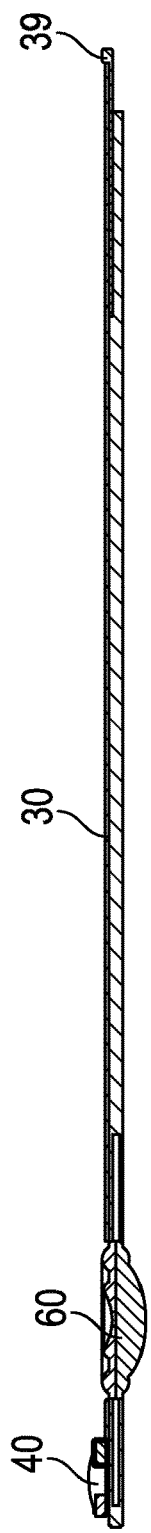
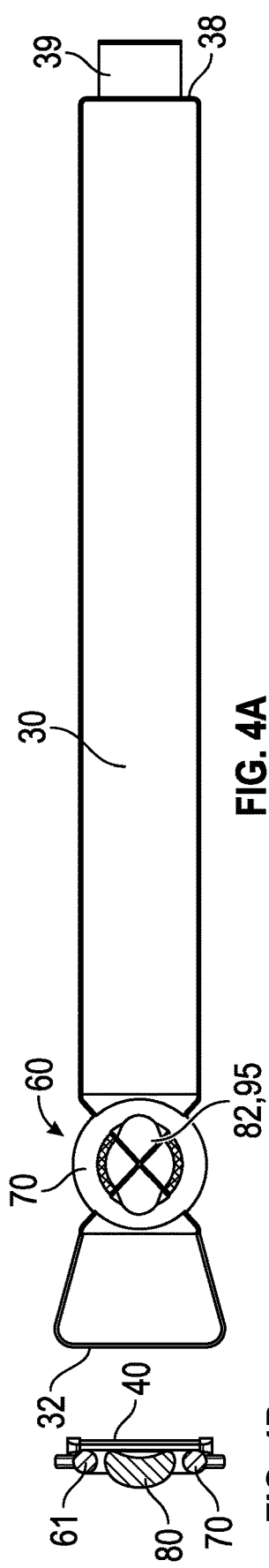
FIG. 3A
FIG. 3B
FIG. 4A
FIG. 4B

EPICONDYLITIS SUPPORT

CROSS-REFERENCE TO RELATED APPLICATIONS

This application claims the benefit of U.S. Provisional Patent Application 63/039,920, filed on Jun. 16, 2020, and is incorporated herein by reference.

STATEMENT REGARDING FEDERALLY SPONSORED RESEARCH AND DEVELOPMENT

Not Applicable.

FIELD OF THE INVENTION

This invention relates to orthopedic braces, more particularly, to a novel brace affixed around the forearm just below the lateral or medial condyle to treat Tennis Elbow or Golfer's Elbow.

BACKGROUND

The elbow joint is a joint made up of three bones: an upper arm bone (humerus) and the two bones in the forearm (radius and ulna). There are bony bumps at the bottom of the humerus called epicondyles. The bony bump on the outside (lateral side) of the elbow is called the lateral epicondyle. Muscles, ligaments, and tendons hold the elbow joint together. The forearm muscles extend the elbow and fingers. The forearm tendons often called extensors attach the muscles to bone on the lateral epicondyle. The tendon and muscle usually involved in tennis elbow are called the Extensor Carpi Radialis Brevis (ECRB). See FIG. 1.

Tennis elbow (lateral epicondylitis), and Golfer's Elbow (medial epicondylitis) are painful conditions of the elbow caused by overuse or repetitive use trauma. Symptoms include pain on the inside or outside of the elbow when lifting the elbow or hand, pain when twisting the forearm, or when making a fist. The area may be slightly swollen or tender to the touch. If the problem persists, additional symptoms can include stiffness in the elbow or weakness in the hands or elbow.

Tennis Elbow and Golfer's Elbow are both overuse injuries that are caused by any activity that requires repetitive motion of the arm and elbow. The difference between the two conditions lies in where the elbow is inflamed. Tennis elbow is an inflammation of the tendons that join the forearm muscles on the outside of the elbow. Golfer's elbow is an inflammation of the tendons that join the forearm muscles on the inside of the elbow. The forearm muscles and tendons become damaged from overuse—repeating the same motions again and again. This leads to pain and tenderness on the outside or inside of the elbow. These injuries are often associated with sports or occupational in nature. See FIG. 2.

Athletes are not the only people who get tennis elbow. Many people with tennis elbow participate in work or recreational activities that require repetitive and vigorous use of the forearm muscle. Painters, plumbers, and carpenters are particularly prone to developing tennis elbow. Studies have shown that auto workers, cooks, and even butchers get tennis elbow more often than the rest of the population. It is thought that the repetition and weightlifting required in these occupations leads to injury. Epicondylitis can occur without any recognized repetitive injury. This occurrence is called "insidious" or of an unknown cause.

Besides rest, ice, massage therapy, steroid injection, or anti-inflammatory over-the-counter drugs like Ibuprofen or Aspirin, healthcare providers often prescribe the use of a compression support or brace. A wide variety of tennis elbow support devices are known in the art. The term "brace" as used herein means an orthopedic support device that does not immobilize the elbow joint, but instead allows for and/or enhances joint motion and stability. The term "elbow" herein means the elbow of a person to which an elbow support device is affixed. In the case of epicondylitis, a brace is typically worn 1-1.5 inches below (distal to) the source of pain.

Correct compression of the forearm muscles below (distal) to the lateral or medial epicondyle absorbs the forces which are transmitted through the soft tissues to the point of pain on the outside or inside of the elbow. They also change the angle at which the tendon works at the elbow which changes the forces which are applied to the tendon attachment allowing the injured area time to recover and reducing pain and inflammation, especially during load bearing tasks. Incorrect compression can damage the radial nerve, create a tourniquet effect, and exacerbate the injury. Therefore, locating and cinching the brace correctly, keeping it in place, and not overtightening the counterforce strap are key to optimal brace function and comfort.

Another proven method to help relieve pain and speed healing of epicondylitis is deep tissue massage. Deep tissue massage to the forearm is a very effective method of easing tennis elbow and healing it much faster than rest alone. Deep tissue massage will enhance circulation and combining this with friction therapy to the tendons on the elbow joint, positive results are seen. Friction therapy breaks down the tension in the tendons, while deep tissue massage techniques will break up scar tissue, alleviate pain, release muscle spasms, and improve flexibility.

User-applied orthopedic support devices are generally differentiated by (1) sleeve (aka pull-on), versus wrap, structure, (2) brace versus splint structure, (3) user adjustability of the brace, (4) limitations on joint motion when wearing the brace, (5) durability, particularly when used in the context of load-bearing or intense repetitive elbow activities, (6) manufacturability, and (7) fastening means (e.g., D-ring, re-closable fasteners, straps and slits, lacing, clasps, snaps, buttons, hooks, rivets, and buckles). "Mating-halves" with re-closable fasteners include hook and loop fasteners, e.g., Velcro® [Registered Trademark]. fasteners (Velcro Industries, Brampton, ON), and mushroom head fasteners, e.g., 3M® Dual Lock fasteners (3M, St. Paul, Minn.).

To prevent, or to ameliorate, epicondylitis pain, a tennis elbow brace is typically prescribed by a clinician or adopted sua sponte by the person. The purpose of the brace is to redirect the pressure over one's muscles so that the injured area does not take the full force. Some elbow braces are designed with adjustable compression. This allows you to determine where and how much pressure to apply to promote healing without restricting blood flow. Conventional braces can do more harm than good if overtightened, creating a tourniquet effect restricting blood flow and risking damage to the radial nerve. The deficiency of conventional tennis elbow braces when used for therapeutic benefit include inadequate compression of the forearm muscles, complexity of fastening, means of proper location, and migration of the brace during wear (i.e., the brace moves around on the forearm and out of the optimal therapeutic position).

Because they can be difficult to don and doff, bulky, uncomfortable, and limiting to normal range of motion, the effectiveness of tennis elbow braces can be severely limited by person non-compliance. When persons choose to stop using a product because of discomfort, limited motion, confusion over how to wear the product properly, or inconvenience, the therapeutic benefits are lost.

The present invention expressly addresses the segment of elbow pain located at the epicondyles (lateral and/or medial), i.e., pain associated with epicondylitis (aka Tennis Elbow or Golfer's Elbow). The present invention also expressly addresses the segment of epicondylitis instability, i.e., local tenderness directly over the lateral and/or medial epicondyle, pain aggravated by resisted wrist extension, pain aggravated by strong gripping or decreased grip strength. The present invention also expressly addresses the segment of prophylactic bracing in high risk environments (i.e., repetitive impact, excessive load-bearing, or vibration from occupational and sports activities) to prevent elbow injury.

There are a limited number of commercially available orthopedic elbow braces which specifically address epicondylitis problems.

The problem to be solved is to provide a tennis elbow and golfer's elbow support device that does not irritate or compress the radial nerve, provides adjustable compression to the area surrounding the forearm, provides adjustment for load-bearing tasks and comfort, fits either the right or left arm, reduces the likelihood of creating a tourniquet effect, is easy to properly locate, does not migrate on the arm during active use, and allows donning and doffing using one hand. It would be further desirable for the solution to this problem to be washable, durable, accommodate a range of forearm circumferences, and support various types of user activity (e.g., playing sports, or during office, factory, or construction work). It would be further desirable for the solution to this problem to include features that prophylactically reduce or eliminate the effect of repetitive use trauma from impact, or heavy loading. It would be further desirable for the solution to this problem to provide means of deep tissue massage to the muscles of the forearm. The present invention accomplishes these objectives.

SUMMARY OF THE INVENTION

The present invention, a tennis elbow and golfer's elbow brace with a soft molded buttress, does not restrict blood flow, does not irritate or compress the radial nerve, provides adjustable compression targeted to the areas distal to the lateral or medial epicondyles of the elbow, provides adequate support through repetitive loading, is used with equal benefit on either the right or left arm, can be doffed and donned with one hand using a single strap fastening mechanism, is easily adjustable for load-bearing tasks and/or comfort, does not migrate on the forearm during active use, and provides the means of a self-applied deep tissue massage. A preferred embodiment avoids the use of fastening mechanisms that are difficult to use and/or that negatively impact the usability of the solution such as slits cut into the fabric of the brace, lacing, clasps, snaps, buttons, hooks, rivets, and buckles. A preferred embodiment further includes a means by which a person can easily position the soft buttress correctly even though the convex bottom face of the buttress is hidden from view. The present invention is washable and durable and accommodates a range of forearm circumferences and types of user activity.

A preferred embodiment further includes a soft molded buttress featuring a convex bottom face and concave top face made of a cushioning material (such as a medical grade silicon with a durometer of 5 to 40 Shore A) which is designed to apply a directed pressure force without irritation, contusion, and/or laceration in the area distal to the epicondyles of the elbow. The purpose of the convex bottom of the buttress is to provide targeted compression without overtightening. The purpose of the concave top face with concentric toric ring, provides an intuitive visual clue, allowing for proper placement (even though the convex shape is hidden from view) and convenient means of self-applied deep tissue massage.

A basic embodiment of the tennis elbow brace comprises a padded counterforce strap assembly adapted to wrap around the forearm area of a person without restricting blood flow. The strap assembly includes a soft molded buttress that allows for proper positioning and targeted compression. A hook-and-loop closure, and a D-ring enable the strap to be fastened and adjusted easily. The targeted compression applied by the molded buttress and counterforce strap reduces the need to wear the brace with excessive tightness and likelihood of a person overtightening the brace which may cause a tourniquet effect and associated arm irritation, bruising, laceration, etc. The molded buttress is optionally constructed of a material that provides a high friction coefficient against the person's skin which helps keep the brace in place during activity. The strap material is optionally a washable material. The strap material is optionally a breathable material.

The tennis elbow brace can be donned using a hook-and-loop fastener. In an example embodiment, a person places the strap assembly on their elbow with the D-ring pointing away from the body toward the pinky side of the arm and with the elastomeric buttress centered about 1-1.5 inches below (distal to) the lateral or medial epicondyle. The person guides the end of the strap though a D-ring using their free hand and pulls the strap upward to tighten the tennis elbow brace around the forearm area. Then while maintaining the strap tension, firmly pressing the mating portion of the strap end to the mating portion on the top surface of the strap assembly. The strap assembly can be tensioned to apply a sufficient and uniform circumferential compressive force on the forearm muscles and specifically targeted alignment forces distal to the lateral or medial side the epicondyle. The compressive and alignment forces of the tennis elbow brace can be easily and rapidly adjusted by pulling the end strap off the mating portion, retensioning the strap, and firmly pressing the end strap to the mating portion on the top surface of the strap assembly.

Once fitted with the tennis elbow brace, persons report decreased pain at rest, decreased pain with grip, decreased pain during activity, and increased function. In addition, use of the tennis elbow brace provides a substantial improvement in person's grip and weight bearing strength. The rehabilitative effects of the tennis elbow brace can be increased by utilizing the optional deep tissue massage feature. The tennis elbow brace is typically worn off-and-on or continuously for weeks, has been enthusiastically adopted by persons, and is reported to be comfortable throughout such continuous use. In certain cases, such as post recovery from an elbow injury, the tennis elbow brace is used to prevent future elbow injuries. Lastly, the strength and durability of the brace has been proven in intense repetitive elbow activities such as tennis, bowling, and hockey, as well as factory, office, and construction work.

DESCRIPTION OF THE DRAWINGS

FIG. 3A is a top plan view of the invention;

FIG. 3B is a cross-sectional view of the invention, taken along lines 3B-3B of FIG. 3A;

FIG. 4A is a bottom plan view of the invention;

FIG. 4B is a cross-sectional view of the invention, taken along lines 4B-4B of FIG. 4A;

DETAILED DESCRIPTION OF THE PREFERRED EMBODIMENT

Figure 1:
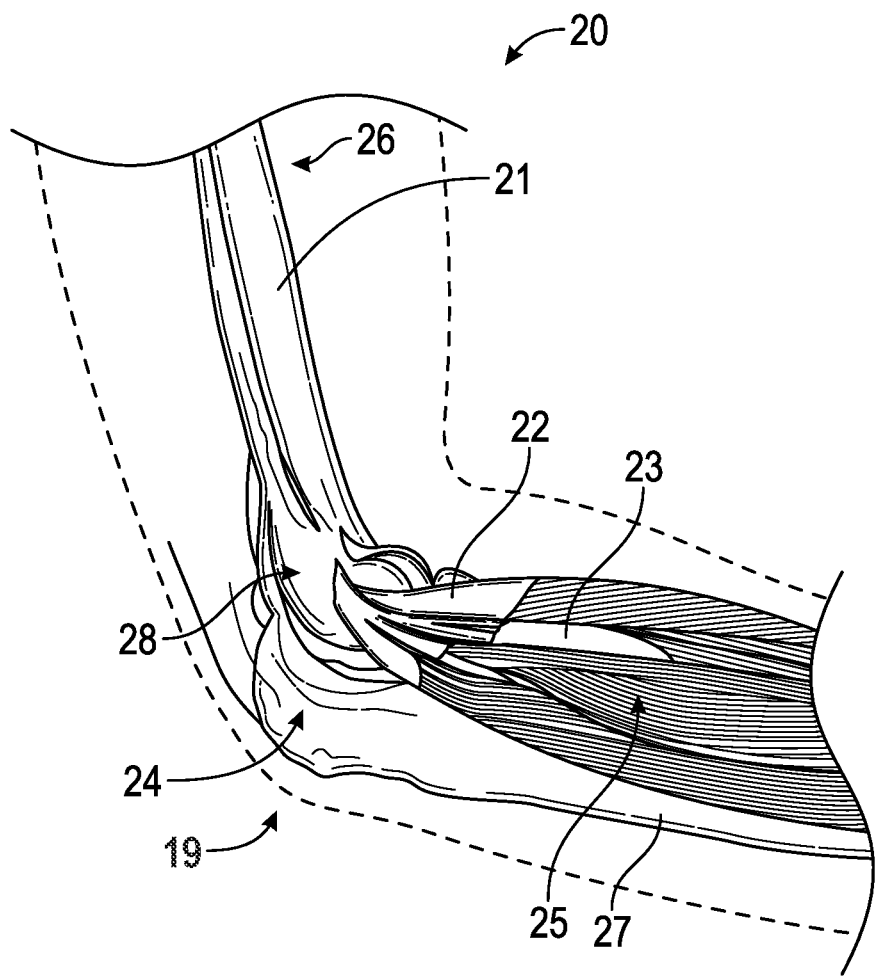
FIG. 1 is a perspective illustration of the anatomy of a human arm.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

FIGS. 3A-4B illustrate an epicondylitis brace assembly 10 for providing therapy to either a medial epicondyle 28 or a lateral epicondyle 29 of an elbow 19 of a person 20. The person 20 further has a humerus 21, extensor tendons 22, an extensor carpi radialis brevis (ECRB) 23, an olecranon 24, forearm muscles 25 in a forearm 26, and an ulna 27.

The epicondylitis brace assembly 10 comprising a flexible band 30 having a first end 32 and a second end 38, and a width $W_1$ between two opposing side edges 35. In some embodiments the second end 38 of the flexible band 30 terminates at a flexible tab 39.

A D-ring 40 is fixed with the first end 32 of the flexible band 30 and adapted to receive the second end 38 therethrough. The flexible band 30 has a two-part mechanical fastener 50 having a first-part 51 thereof fixed proximate the first end 32 of the flexible band 30, and a second-part 52 of the two-part mechanical fastener 50 being fixed with the flexible band 30 adjacent the first-part 32 of the two-part mechanical fastener 30. Preferably the first-part 51 of the two-part mechanical fastener 50 includes a hook-material, and the second-part 52 of the two-part mechanical fastener 50 includes a loop material, the two-part mechanical fastener 50 being a hook-and-loop type fastening material.

An elastomeric buttress 60 is fixed with the flexible band 30 proximate the D-ring 40, the D-ring 40 being disposed between the elastomeric buttress 60 and the first end 32 of the flexible band 30. The elastomeric buttress 60 includes an open mesh 61 having two opposing ends 65, a central ring 70 fixed with each end 65 and having a central area 75, and a central nodule 80 fixed within the central area 75 and with a preferably inelastic open mesh 61. The central nodule 80 comprises a top side 88 with a concave actuator 90 and a bottom side 82 with a complex convex surface 95 (FIGS. 5-8B) whereby with the epicondylitis brace assembly 10 fixed about the person's elbow 19, wherein the complex convex surface contacts either the person's medial epicondyle 28 or the person's lateral epicondyle 29, pressure is applied to either the medial epicondyle 28 or a lateral epicondyle 29 by the force of the open mesh 61. Additional pressure can be applied to the actuator 90 manually to cause the complex convex surface 95 to apply the additional pressure to either the medial epicondyle 28 or the lateral epicondyle 29. In some embodiments the complex convex surface 95 is an ovaloid. Alternately, the complex convex surface 95 is a first ovaloid 96 in a direction aligned with a longitudinal axis of the flexible band 30, and further includes a second smaller ovaloid 97 orthogonal in a long dimension to that of the first ovaloid.

In use, when the person 20 dons the epicondylitis brace assembly 10 with the elastomeric buttress 60 fixed at the either the medial epicondyle 28 or the lateral epicondyle 29, pressure is applied to either the medial epicondyle 28 or the lateral epicondyle 29.

Figure 2:
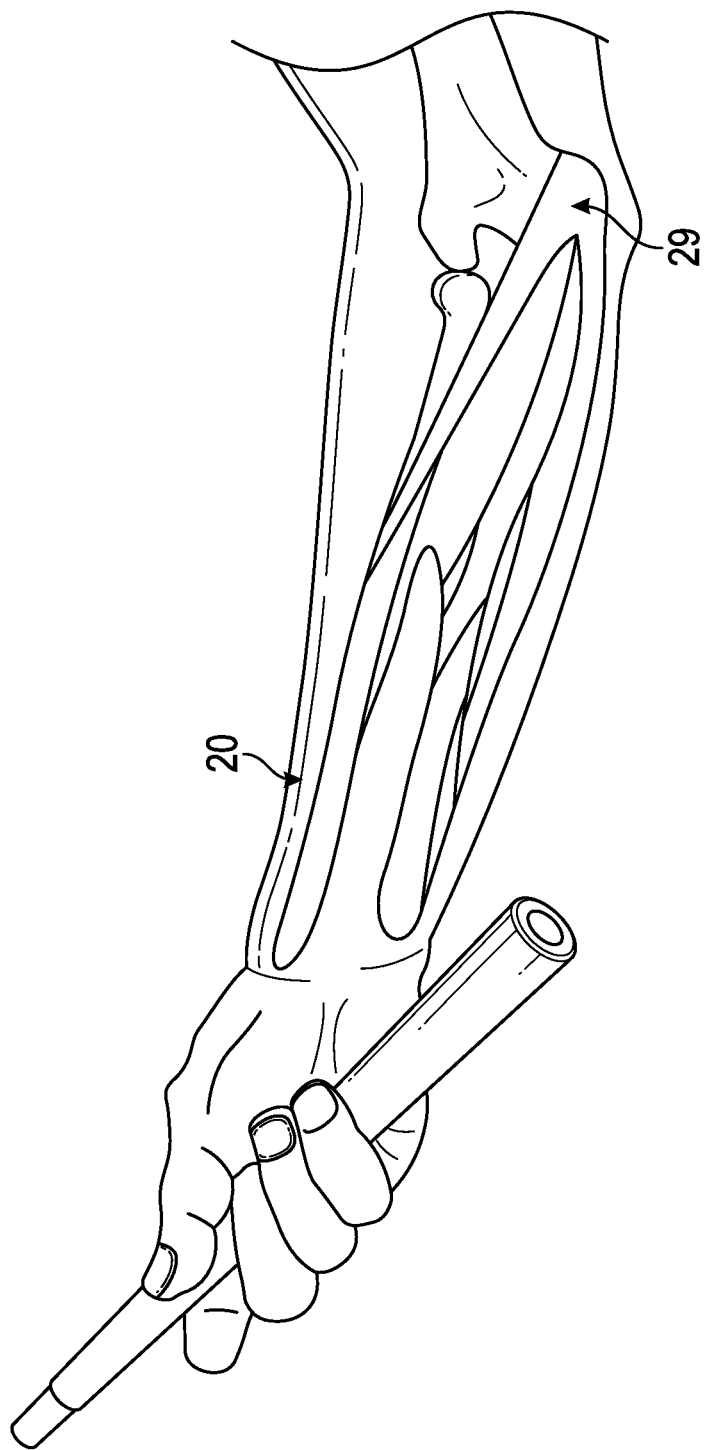
FIG. 2 is an alternate perspective illustration of the anatomy of the arm.
Figure 5:
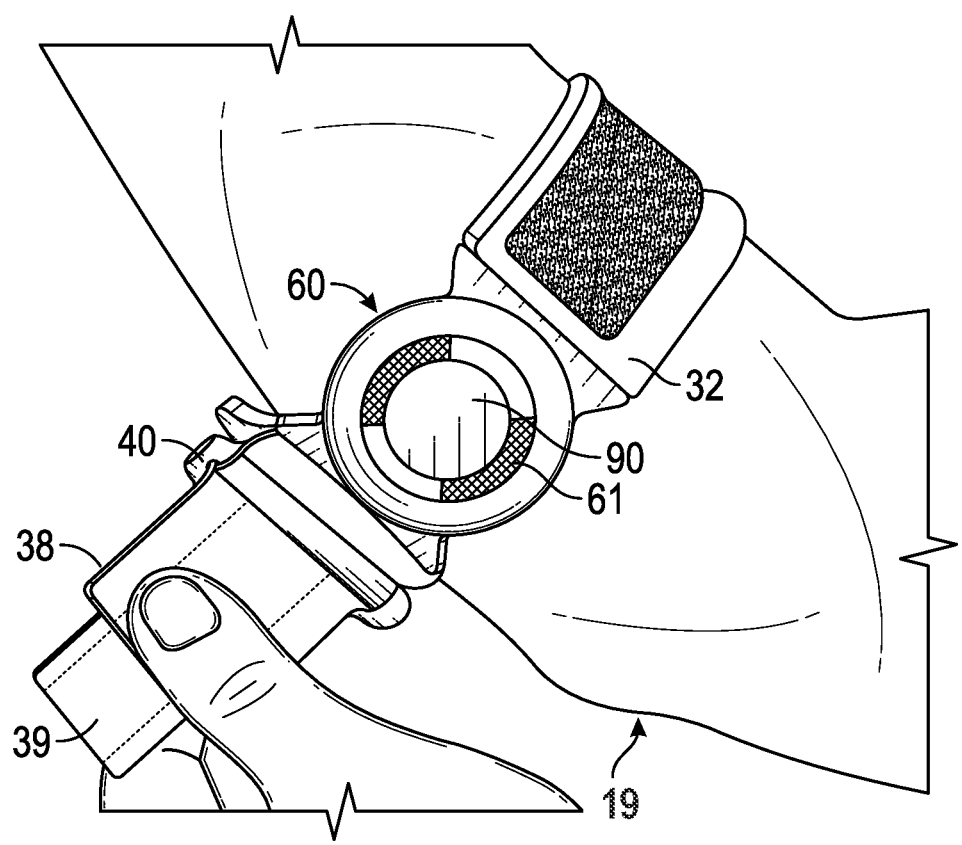
FIG. 5 is a perspective view of the invention, illustrated while being fixed to a human arm.
Figure 6:
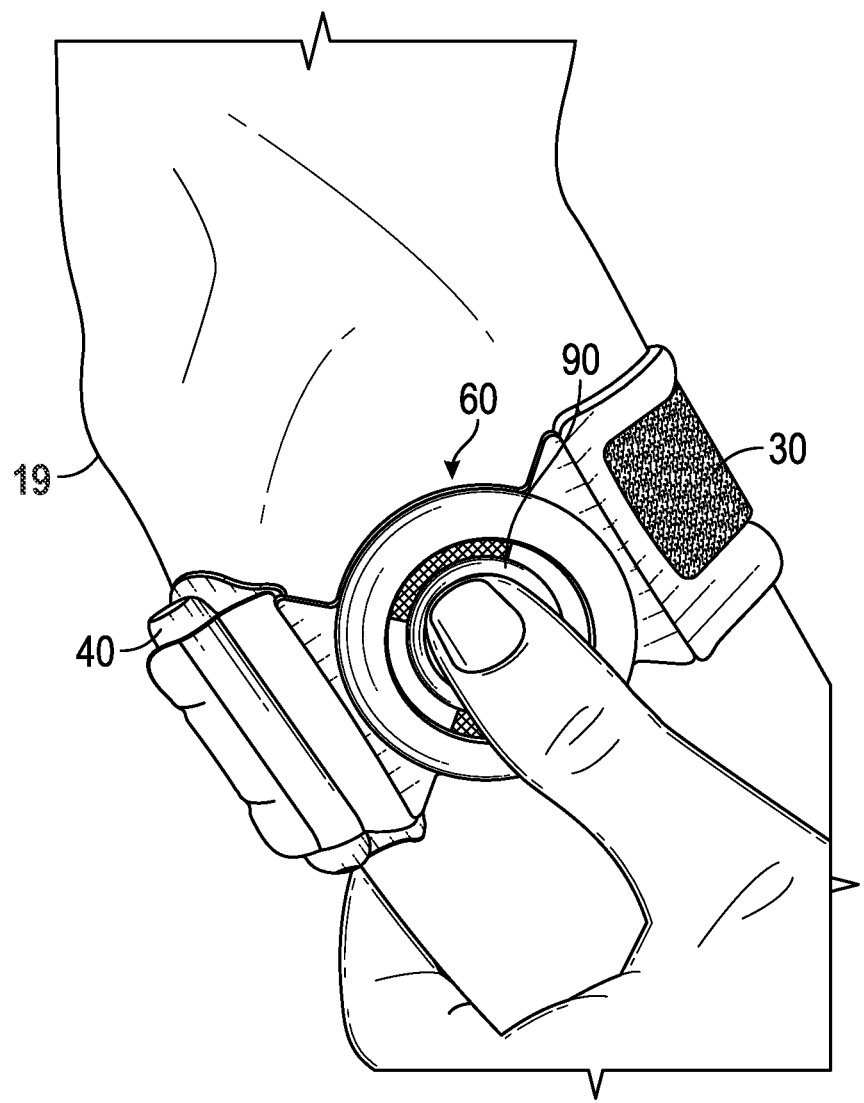
FIG. 6 is a perspective view of the invention, illustrated with pressure being applied to concavity centered inside an elastomeric buttress of the invention.

An exemplary Epicondylitis brace assembly 10 is to be worn a predetermined distance, such as 1-1.5 inches, below or distal to the elbow of the person 20 for stabilizing the elbow joint and preventing or relieving pain and discomfort associated with epicondylitis, as shown in FIGS. 5 & 6. A basic embodiment of the epicondylitis brace assembly 10 includes the flexible band 30 being adapted to wrap around the left or right elbow 19 (FIGS. 1 and 2) of a person 20 including at least a portion of forearm muscles 25 in an ECRB area 23 (FIG. 1).

The elastomeric buttress 60 in some embodiments is over-molded or attached by other means to the band 30. The elastomeric buttress 60 can be made of an elastomer, such as medical grade silicone with a 5-30 durometer Shore A, and shaped to apply targeted/controlled compression to the ECRB 27. A non-deformed shape of the elastomeric buttress 60 can be, for example, round, elliptical, oval, ovoid, or other suitable shape, and can be provided in different sizes for different size elbows.

The width $W_1$ of the flexible band 30 is typically 4.5 to 7.0 cm in width. Optionally, the epicondylitis brace assembly 10 has embedded or affixed branding. In an example branding embodiment, the flexible tab 39 is optionally affixed to the epicondylitis brace assembly 10, as illustrated in FIG. 5.

An exemplary means to "don" such a epicondylitis brace assembly 10 corresponds to a process of: (A) inserting the second end 38 of the flexible band 30 through D-ring 40 (a U-shape is formed by the second end 38 as it passes through the D-ring 40 and back toward the flexible band 30; (B)

sliding a person's hand and elbow 19 through a loop of the flexible band formed by the second end 38 traversing the D-ring 40; (C) pressing the two parts 51,52 of the two-part mechanical fastener 50 together; (D) retensioning the flexible band 30 by pulling second end 38 further through the D-ring 40; and (E) re-fastening the second end 38, still under tension, to the mating half of the two-part mechanical fastener 50. The orientation of the epicondylitis brace assembly 10 may also be adjusted by the person 20 during the retensioning step D to provide a maximum reduction of pain in the epicondylitis 28,29 area. With proper donning, the flexible band 30 clears an elbow crease and allows full flexion and extension of the elbow 19 without irritation to the elbow 19.

An exemplary means to "doff" the epicondylitis brace assembly 10 corresponds to a process of: (A) loosening the second end 38 of the flexible band 30 by separating the two-part mechanical fastener 50; (B) expanding a circumference of the epicondylitis brace assembly 10 by pulling the flexible band 30 outward away from the elbow 19, causing a portion of the flexible band 30 to be pulled through the D-ring 40; and (C) withdrawing the person's forearm 26 from the epicondylitis brace assembly 10. Alternatively, in step B, a portion of the flexible band 30 can be pushed through the D-ring 40 to expand the circumference of the flexible band 30.

The two-part mechanical fastener 50 may be a hook and loop material, or a "mushroom head" material (not shown). The first-part 51 of the two-part mechanical fastener 50 is affixed to second end 38 of the flexible band 30 so that when the second end 38 of the flexible band 30 is threaded through D-ring 40 and pulled back towards the flexible band to tension the flexible band 30 (e.g., to form a U around D-ring 40), each part 51,52 of the two-part mechanical fastener 50 can mutually engage, and while engaged, maintain a flexible band 30 tension. Such two-part mechanical fasteners 50 are preferred fastening means in view of their ease of fastening and adjustment of the flexible band 30.

Adults forearms 26 vary in circumference from 8 to 16 in. The flexible band 30 interfaces with or contacts the person's forearm 26, as well as the elastomeric buttress 60, and both are optionally configured with various lengths and widths corresponding to various sizes (e.g., extra-small, small, medium, large, extra-large, adult small, child small, Medium with Large width, Large with Medium width, etc.). In an example embodiment, a medium size flexible band 30 is 14.2 in (including the D-ring 40 extending from flexible band 30). Dimensions of pediatric sizes bands 30 are proportionally smaller.

The flexible band 30 optionally has a width $W_1$ of between 1 to 2.5 in. The width $W_1$ may optionally vary from 0.25 to 0.50 in to accommodate various sizes for various persons and associated elbow conditions. Optionally, the width $W_1$ of the flexible band 30 can taper outward in various sizes to accommodate different sizes of elastomeric buttresses 60 (not shown). Preferably, the D-ring 40 varies in size from about 1.5 inches to 2.0 inches, or at least sufficient to accommodate the flexible band 30.

The flexible band 30 optionally comprises a padded material. The flexible band 30 can be made, for example, from a padded strap of material that is folded and attached to form a flattened tube, such that padding is completely enclosed by an external material (e.g., stitch-and-turned into a tubular shape with no sharp edges, not shown). The flexible band 30 and/or flexible band 30 external material can be selected from materials that are naturally or artificially hypoallergenic and non-abrasive against the skin of the elbow 19. The external material can also be selected to provide a desired combination of smoothness, such that the epicondylitis brace assembly 10 can easily slide over the elbow 19 before fastening, while providing sufficient friction such that the epicondylitis brace assembly 10 can be tensioned and fastened around the elbow 19 during donning. Advantageously, the ulnar head 27 contacting the elastomeric buttress 60 also provides resistance during donning. Optionally, the flexible band 30 measures 3 to 8 mm in thickness. In an example embodiment, the flexible band 30 measures 2 mm thick.

The flexible band 30 is optionally configured in various lengths and widths. Generally, the width of second end 38 of the flexible band 30 does not exceed the width $W_1$ of flexible band 30. The width and/or length of the second end 38 is configured to provide sufficient mating force to ensure the epicondylitis brace assembly 10 does not separate during certain elbow activities at the two-part mechanical fastener 50. Optionally, additional fastening mating area (not shown) may be configured in active and/or load bearing targeted epicondylitis braces 10. Optionally, a smaller second end 38 width and/or length may simplify manufacturing and reduce material costs, while still being capable of maintain tension in the flexible band 30. In an example embodiment, the second end 38 of the flexible band 30 is configured/constructed with lengths of 18 cm, 22 cm, and 27.3 cm corresponding to a small, medium, and large sized epicondylitis brace assembly 10, respectively.

Optionally, the dimension of the epicondylitis brace D-ring 40 is configured/constructed slightly larger than the width of the second end 38 of the flexible band 30. This enables a modest amount of friction between the second end 38 of the flexible band 30 and the D-ring 40 to reduce slippage when creating a loop of the flexible band 30 with the D-ring 40 as described in the "donning" process, step A above. Optionally, the D-ring 40 is sewn into the first end 32 of the flexible band 30 using a bar tack or other linear stitch with the joining material folded inward or otherwise hidden from view so as to create a finished edge. Optionally, D-ring 40 is attached to the first end 32 of the flexible band 30 using another fixation method such as sonic welding, heat bonding, or through means of an adhesive compound. Optionally, D-ring 40 is configured not to protrude over the first end 32 of the flexible band 30. Optionally, the D-ring 40 is configured to extend over the flexible band 30 (e.g., as illustrated in FIG. 5) to simplify donning as the person 20 does not have to lift the D-ring 40 away from the flexible band 30 during the initial insertion of flexible band 30. Advantageously, an extended D-ring 40 and a sufficiently configured flexible band 30 length, the second end 38 of the flexible band 30 is isolated from and does not interface with the elbow 19 of the person 20. As such, the second end 38 of the flexible band 30 is optionally made of a different material from the flexible band 30 and may be more or less durable, more or less elastic, be of a different width, and cost less to source and/or manufacture. Optionally, the epicondylitis brace assembly 10 does not include the D-ring 40 but rather is inserted through a cutout in the flexible band 30 (not shown). In this case, the second end 38 of the flexible band 30 interfaces with the person's elbow 19 and does not have the advantages previously described.

The elastomeric buttress 60 which forms a cushioned border around the medial epicondyle 28 or the lateral epicondyle 29, and is designed to apply a directed pressure force without irritation, contusion, and/or laceration in the area in close proximity to the ECRB 23. A diameter of the convex hemisphere/ovaloid shape is configurable. Optionally, a greater diameter hemisphere/ellipsoid is used in larger sizes and a smaller diameter hemisphere/ovaloid is used in smaller sizes to fit various sized forearms. An outside diameter of the toric ring 60 generally ranges from 3 cm to 4 cm (FIGS. 7A-8B).

It is preferable that the elastomeric buttress 60 be positioned on the flexible band 30 in close proximity to the D-ring 40. When flexible band 30 is tensioned during donning, the effect of the tension force is greatest near the D-ring 40. Therefore, positioning the elastomeric buttress 60 nearest to the D-ring 40 enables a person 20 to achieve a comfortable tension around the forearm 27 without unnecessary flexible band 30 tension outside of the epicondylitis regions 28,29. In addition, placement of the elastomeric buttress 60 in close proximity to the D-ring 40 enables a maximal mating surface and size of the second end 38 of the flexible band 30 as illustrated in FIG. 3A. Advantageously, such a maximal mating surface extends the life of the epicondylitis brace assembly 10, particularly in active and/or load bearing scenarios.

Figure 8A:
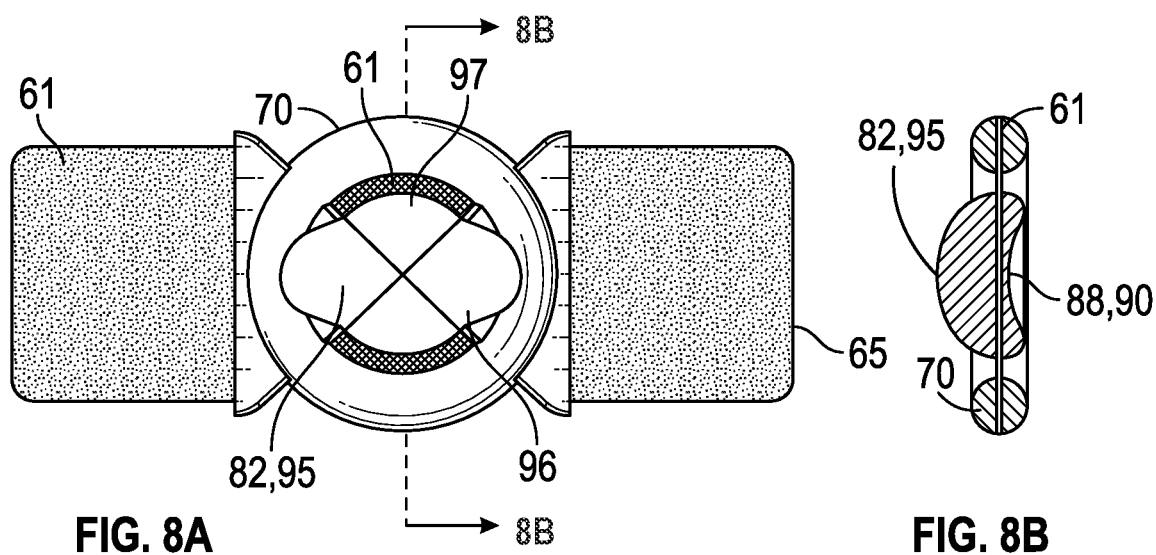
FIG. 8A is a bottom plan view of FIG. 7A.
Figure 8B:
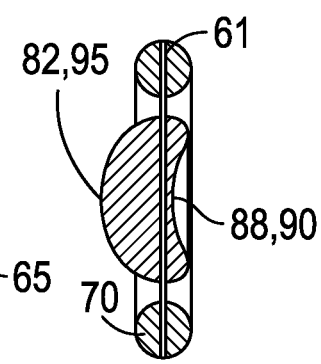
FIG. 8B is a cross-sectional view of the elastomeric buttress, taken along line 8B-8B of FIG. 8A.

In a preferred embodiment, the elastomeric buttress 60 is made of a cushioning material (such as a medical grade silicon with a durometer of 5 to 40 Shore A) and is reinforced with the central nodule 80, as illustrated in FIG. 8. In an example embodiment, the elastomeric buttress 60 and central nodule 80 are manufactured integrally from the same material and as a single part. The central nodule 80 is pre-molded over and through a preferably inelastic open mesh 61, such as nylon or acetal mesh fabric. After the central nodule 80 is pre-molded into the open mesh 61, the elastomeric buttress 60 and associated central nodule 80 can be readily sewn to the flexible band 30, or otherwise incorporated into the flexible band 30 by known methods. The central nodule 80 can be made of medical grade silicone, silicone, plastic, or other material that can increase the stiffness of the flexible band 30 without adding much weight, such that the epicondylitis brace assembly 10 remains flexible while retaining its shape over extended use, after washing, etc. Silicone is an ideal cushioning material because it will not "bottom-out," is relatively durable, and is hypoallergenic. The high-density of silicone offers unique cushioning without excess bulk. Silicone also exhibits superior moldability.

It is preferable that the elastomeric buttress 60 be deformed into an oval shape so that the forces exerted through the elastomeric buttress 60 by the flexible band 30 should be well on the lateral side of the ulna 27 and not on the volar side where the sensitive ulnar styloid process is located. When the epicondylitis brace assembly 10 is properly tensioned, the shape of the elastomeric buttress 60 will deform from a circle into an oval shape. Optionally, the elastomeric buttress 60 is oval shaped to align the compression of the elastomeric buttress 60 on the lateral side of the ulna 27. Optionally, the oval shape elastomeric buttress 60 is subject to modest deformation during tensioning. A non-ovoid shape is counter-productive because it causes compression the ulnar styloid process.

FIG. 3A illustrates a top view of an example embodiment of an epicondylitis brace assembly 10 constructed with a flexible band 30, an elastomeric buttress 60, and equipped with a D-ring 40 and the two-part mechanical fastener 50. In some example embodiments, a taper may be included with the flexible band 30 from the first end 32 to the second end 38, to accommodate the elastomeric buttress 60 in a smaller width epicondylitis brace assembly 10.

Figure 7A:
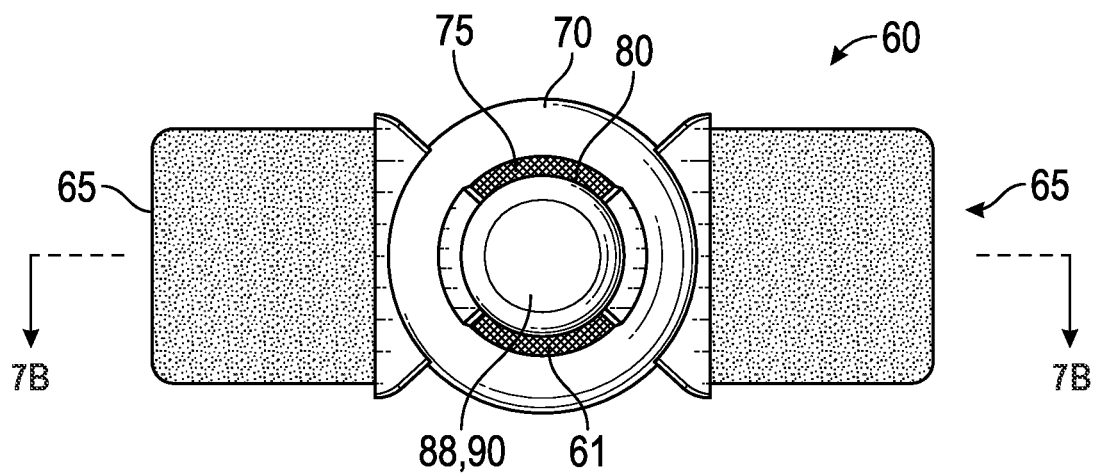
FIG. 7A is a top plan view of the elastomeric buttress of the invention, a flexible band of the invention omitted for clarity of illustration.
Figure 7B:
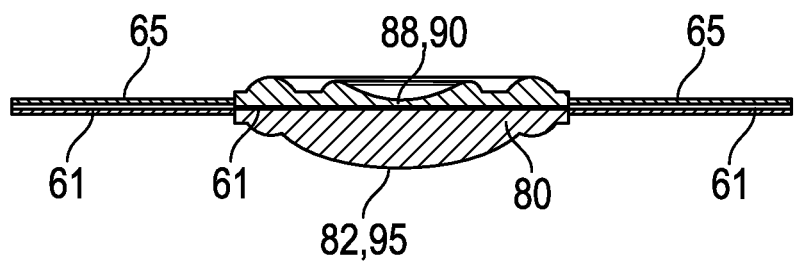
FIG. 7B is a cross-sectional view of the elastomeric buttress, taken along line 7B-7B of FIG. 7A.

FIG. 7A illustrates an example embodiment of an elastomeric buttress 60 with the central nodule 80.

The flexible band 30 is typically a washable, inelastic, woven textile. The bottom of a textile flexible band 30 may be woven or constructed to create a soft surface, e.g., woven pile, finishing by knapping or abrasion.

The flexible band 30 can be made from various types of flexible, non-elastic, cushioned material. Various means known in the art of attachment of mating-halves reclosable fasteners such as the D-ring 40 and elastomeric buttress 60 can be used, e.g., sewing, adhesives, sonic welding, heat welding, and heat fusion. The type of material is selected for its elastomeric, tactile, breathability, weight, hypoallergenic, and durability properties. The flexible band 30 can be constructed to have finished edges 35 with no visible cut edges and a soft-feeling interior surface that has non-slip properties. In a preferred embodiment, spacer fabric (not shown) such as a textile constructed of vertical fibers is used to provide cushioning similar, or better than, foam but in a much less dense and more breathable material.

Further with respect to the construction and/or manufacture of the epicondylitis brace assembly 10, two conventional molding methods include: (1) over-molding silicone onto a pre-sewn flexible band 30, (2) compression molding foam onto a pre-sewn flexible band 30. Disadvantageously, these methods create cost and quality issues as these processes are generally subject to assembly challenges. For example, rejects can happen due to delamination and fabric damage due to high temperature and pressure, and it is difficult to achieve the proper durometer and deformation characteristics. In a preferred manufacturing embodiment, a first step is to pre-mold a cushioning material (for example, medical grade silicone, 5-40 Shore A durometer) of the elastomeric buttress 60 over and through an inelastic open mesh 61 of the flexible band 30. The open mesh 61 is as "open" as possible (for example, 1-3 mm in diameter) to enable the cushioning material to flow through and encapsulate the open mesh 61 to prevent delamination but also strong and inelastic to prevent the elastomeric buttress 60 from elongating excessively during tensioning. In a preferred embodiment, the range of elongation of the diameter of the elastomeric buttress 60 is between 3-6 mm when 1-3 kg longitudinal force is applied (to simulate the typical force applied when donning the brace). In a preferred embodiment, the open mesh 61 is constructed from materials such as nylon or acetal mesh to withstand molding pressure and high temperature during the pre-molding process. Optionally the open mesh 61 may be an elastic mesh that is pre-stretched before molding. In some embodiments the open mesh 61 is a flexible metallic screen material or other mesh material.

Subsequent to the elastomeric buttress 60 being pre-molded onto the open mesh 61, it can be readily sewn to the padded flexible band 30. This method of manufacturing of epicondylitis brace assembly 10 has shown to reduce quality rejects in manufacturing by 60-90 percent over conventional methods of over-molding or compression molding described above. The preferred manufacturing method also reduces manufacturing time and cost as compared to the over-molding or compression molding techniques. Encapsulating the open mesh 61 within the elastomeric buttress 60 allows for sewing of the molded silicon material to the flexible band 30 without tearing of the silicon material, as well as inhibiting stretching of the silicon material while still providing flexibility. During the molding process the silicon material flows through gaps in the open mesh 61, which isn't easily possible with a non-mesh material.

The materials used for the flexible band 30 is selected as a function of elasticity, thickness, flexibility, ease of handling during manufacturing, cost, breathability, ease of donning, doffing, and washing, and person comfort. The materials comprising the flexible band 30 is not so flexible that the materials deform excessively in a direction parallel to that of the person's forearm 26. Embodiments of the epicondylitis brace assembly 10 for the health care market would typically be manufactured with higher quality textile materials. "Higher quality textile materials" means very minor deviations in elasticity, thickness, and flexibility over time and material lots, easier to handling during manufacturing, very breathable, easy to don and doff, stable after multiple washes, and comfortable to wear for long periods, e.g., continuously for six weeks.

Embodiments made of lower quality materials, such as injection molded plastics, have a lower cost of manufacturing and may be correspondingly priced at a lower point. Lower quality materials such as foam laminates have greater deviations in elasticity, thickness, and flexibility over time and material lots, are harder to handle during manufacturing, may have poor or zero breathability, are more difficult to don and doff, can delaminate, can cause allergic reactions to lamination adhesives, are subject to loss of stability after multiple washes, and are less comfortable to wear for long periods.

The length of the flexible band 30 can be dimensioned to create various sizes (e.g., small, medium, large, and other sizes) of a epicondylitis brace assembly 10; the approximate length of the strap of an example embodiment small, medium, and large size is 22 to 28 cm, 30 to 34 cm, and 40 to 44 cm, respectively. Having a unilateral, "one size fits either elbow", size has significant manufacturing, distribution, and stocking advantages. The length described here is to accommodate a range of average human forearm u circumferences.

Although the epicondylitis brace assembly 10 can be custom-made for a specific forearm area circumference, i.e., made with one position fasteners, such embodiments deprive a person 20 of the ability to adjust the compressive force of the epicondylitis brace assembly 10 to reflect a given task or activity. For instance, more compressive force would be needed when bowling than when sleeping.

Generally, the flexible band 30 and the elastomeric buttress 60 of the epicondylitis brace assembly 10 allow it to accommodate a wide range of anthropometric variation in the epicondylitis area without the need of multiple sizes of the epicondylitis brace assemblies 10. Optionally, only pediatric and adult sizes of the epicondylitis brace assembly 10 may be stocked in inventory.

FIG. 3B shows a longitudinal cross-section view of a donned example embodiment epicondylitis brace assembly 10. The two parts 51,52 of the hook and loop fastener 50 can mutually engage, thereby maintaining the flexible band 30 in a tensioned state and thereby maintaining centripetal compression of the forearm area 26. The second end 38 of the flexible band 30, when folded over in a properly sized epicondylitis brace assembly 10, reaches approximately halfway around the flexible band 30 at the second end 38.

FIGS. 5-6 illustrate a perspective view of a first way of wearing an example embodiment epicondylitis brace assembly 10. As shown in FIG. 5, to use a epicondylitis brace assembly 10 with hook/loop fastening means 50, the person typically guides the second end 38 of the flexible band 30 through the D-ring 40 at the end of flexible band 30 in order to configure the epicondylitis brace assembly 10 as a cylinder with a protruding second end 38. The epicondylitis brace assembly 10 is slipped over the person's hand and forearm 19 until the elastomeric buttress 60 overlies the ulnar head 27. The person 20 optionally places the dorsal (outside) face of the elastomeric buttress 10 against a flat surface to stabilize the epicondylitis brace assembly 10, pulls the second end 38 of the flexible band 30 medially (i.e., back toward the dorsal face) to tighten the epicondylitis brace assembly 10 around the forearm 26, then firmly presses the bottom of the second end 38 against the corresponding mating portion of the two-part mechanical fastener 50 on a dorsal section of the epicondylitis brace assembly 10. The compressive force of the flexible band 30 can be easily, rapidly, and independently adjusted by pulling the second end 38 off two-part mechanical fastener 50 on the dorsal section, retensioning the flexible band 30, and firmly pressing the bottom of the second end 38 against the corresponding mating portion of the two-part mechanical fastener 50 on the dorsal section of the epicondylitis brace assembly 10.

The person 20 can apply and adjust an epicondylitis brace assembly 10 unilaterally. The cushioned elastomeric buttress 60 conforms closely and comfortably to the contours of the ulnar head 27. The flexible band 30 tension is typically increased for load-bearing tasks and decreased for non-load-bearing tasks. Load-bearing tasks include both work tasks and sports activities, such as tennis, golf, bowling, gardening, and weightlifting. The epicondylitis brace assembly 10 provides adjustable support of the ulnar head 27 and ECRB region 23, decreases epicondylitis associated pain arising from function, work and sports, increases grip strength, provides support through supination and pronation of the elbow 19, increases weight bearing capabilities of the elbow 19, decreases pain with grip, and decreases pain with weight bearing. Prophylactic use helps to prevent epicondylitis injury, and extensor carpi ulnaris subluxation. Post-injury and post-surgery use helps to heal the epicondylitis. Embodiments of the epicondylitis brace assembly 10 optionally can be made using consumer quality materials for retail sales, and higher quality materials for clinical and institutional uses. The epicondylitis brace assembly 10, when made of the preferred materials and washed regularly, avoids skin breakdown or irritation of the skin, even when worn for several weeks. The epicondylitis brace assembly 10 is low profile and does not interfere with elbow motion. The epicondylitis brace assembly 10 can be worn damp and/or wet and will adequately dry with or without removal.

When using the epicondylitis brace assembly 10, the lack of immobilization of elbow flexion and extension allows improved function with less risk. No inclusion of the elbow joint 28 is a key design element and benefit of the epicondylitis brace assembly 10, and avoids risk of stiffness associated with joint immobility.

Diagnoses for which the epicondylitis brace assembly 10 may be used include but are not limited to: Lateral Epicondylitis (Tennis Elbow) and Medial Epicondylitis (Medial Epicondylitis). Prophylactic use of the epicondylitis brace assembly 10 is recommended for prevention of injury for, inter alia, tennis players, golfers, bowlers, and weightlifters, yoga practitioners, factory workers, and carpenters who have a high risk of injury to their elbows.

The two-part mechanical fasteners 50 discussed herein are based on the hook and loop fastener type of technology. In addition to this technology, other fastener technologies may be used in other embodiments including, for example, snaps, pins, or other hook and claw arrangements. Other fastening means may add cost and complexity, however, and may irritate the skin, forearm area, and/or elbow.

Thus, an example embodiment of the epicondylitis brace assembly 10 as described above, advantageously, does not irritate or compress the radial nerve, provides adjustable compression to the ECRB region 23, fits either the right or left elbow, reduces the likelihood of creating a tourniquet effect, and allows donning and doffing using one hand.

The described epicondylitis brace and/or support device is also washable, durable, accommodate a range of forearm circumferences, and support various types of user activity (e.g., sports, office work, construction work, etc.). In addition, features of the epicondylitis brace prophylactically reduce or eliminate the effect of repetitive use trauma from impact, pronation/supination, flexing/extending, or heavy loading. Lastly, the epicondylitis brace assembly 10 avoids the use of difficult-to-apply fasteners and compression methods (e.g., slots cut in fabric through which straps are passed, this type of design serves to lower manufacturing cost at the expense of ease of use as it can be difficult for average people to manage, or especially those with arthritis or otherwise compromised range of motion and dexterity.)

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the invention has been described with reference to specific embodiments thereof, it will be understood that numerous variations, modifications, and additional embodiments are possible, and all such variations, modifications, and embodiments are to be regarded as being within the spirit and scope of the invention.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above.

The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms.

Accordingly, the inventor reserves the right to add additional claims after filing the application to pursue such additional claim forms for other aspects of the invention.

What is claimed is:

1. An epicondylitis brace assembly for providing therapy to either a medial epicondyle or a lateral epicondyle of an elbow of a person, the person further having a humerus, extensor tendons, an extensor carpi radialis brevis (ECRB), an olecranon, forearm muscles in a forearm, and an ulna, the epicondylitis brace assembly comprising:
    a flexible band having a first end and a second end, and a width W between two opposing side edges;
    a D-ring fixed with the first end of the flexible band and adapted to receive the second end therethrough, the flexible band having a two-part mechanical fastener having a first-part thereof fixed proximate the first end of the flexible band, and a second part of the two-part mechanical fastener being fixed with the flexible band adjacent the first part of the two-part mechanical fastener;
    a toric ring fixed with the flexible band proximate the D-ring, the D-ring being disposed between the toric ring and the first end of the flexible band;
    wherein the toric ring includes an open mesh having two opposing ends, a central ring fixed with each of the two opposing ends and having a central area, a central nodule fixed within the central area and with the open mesh, the central nodule comprising a top side with a permanently concave actuator and a bottom side with a complex convex surface, the open mesh being located between the permanently concave actuator and the complex convex surface of the central nodule;
    whereby with the epicondylitis brace assembly fixed about the person's elbow wherein the complex convex surface contacts either the person's medial epicondyle or the person's lateral epicondyle, pressure is applied to either the medial epicondyle or a lateral epicondyle by a force of the open mesh, and additional pressure applied to the permanently concave actuator serves to cause the complex convex surface to apply pressure to either the medial epicondyle or the lateral epicondyle;

whereby when the person dons the epicondylitis brace assembly with the toric ring fixed at either the medial epicondyle or the lateral epicondyle, pressure is applied to either the medial epicondyle or the lateral epicondyle.

2. The epicondylitis brace assembly of claim 1 wherein the second end of the flexible band terminates in a flexible tab.

3. The epicondylitis brace assembly of claim 1 wherein the complex convex surface is an ovaloid.

4. The epicondylitis brace assembly of claim 1 wherein the complex convex surface is a first ovaloid in a direction aligned with a longitudinal axis of the flexible band, and further includes a second smaller ovaloid orthogonal in a long dimension to that of the first ovaloid.

5. The epicondylitis brace assembly of claim 1 wherein the first-part of the two-part mechanical fastener includes a hook-material, and wherein the second-part of the two-part mechanical fastener includes a loop material.

6. The epicondylitis brace assembly of claim 1 wherein the open mesh is an inelastic woven open mesh.

7. The epicondylitis brace assembly of claim 1 wherein the open mesh is an elastic woven open mesh.

8. An epicondylitis brace assembly for providing therapy to either a medial epicondyle or a lateral epicondyle of an elbow of a person, the person further having a humerus, extensor tendons, an extensor carpi radialis brevis (ECRB), an olecranon, forearm muscles in a forearm, and an ulna, the epicondylitis brace assembly comprising:

a flexible band having a first end and a second end, and a width between two opposing side edges, the second end of the flexible band terminating in a flexible tab;

a D-ring fixed with the first end of the flexible band and adapted to receive the second end therethrough, the flexible band having a two-part mechanical fastener having a first-part thereof fixed proximate the first end of the flexible band, and a second part of the two-part mechanical fastener being fixed with the flexible band adjacent the first part of the two-part mechanical fastener;

a toric ring fixed with the flexible band proximate the D-ring, the D-ring being disposed between the toric ring and the first end of the flexible band, the toric ring including a open mesh having two opposing ends, a central ring fixed with each of the two opposing ends and having a central area, a central nodule fixed within the central area and with the open mesh, the central nodule comprising a top side with a concave actuator and a bottom side with a complex convex surface, the complex convex surface being a first ovaloid in a direction aligned with a longitudinal axis of the flexible band, and further including a second smaller ovaloid orthogonal in a long dimension to that of the first ovaloid;

wherein the toric ring includes an open mesh having two opposing ends, a central ring fixed with each of the two opposing ends and having a central area, a central nodule fixed within the central area and with the open mesh, the central nodule comprising a top side with a permanently concave actuator and a bottom side with a complex convex surface, the open mesh being located between the permanently concave actuator and the complex convex surface of the central nodule;

whereby when the person dons the epicondylitis brace assembly with the toric ring fixed at either the medial epicondyle or the lateral epicondyle, pressure is applied to either the medial epicondyle or the lateral epicondyle; and whereby when the epicondylitis brace assembly is fixed about the person's elbow, the complex convex surface contacts either the person's medial epicondyle or the person's lateral epicondyle so that pressure is applied to either the medial epicondyle or a lateral epicondyle by a force of the open mesh, and additional pressure applied to the permanently concave actuator serves to cause the complex convex surface to apply pressure to either the medial epicondyle or the lateral epicondyle.

9. A method for forming an epicondylitis brace assembly for providing therapy to either a medial epicondyle or a lateral epicondyle of an elbow of a person, the person further having a humerus, extensor tendons, an extensor carpi radialis brevis (ECRB), an olecranon, forearm muscles in a forearm, and an ulna, the method comprising the steps:

providing a flexible band having a first end, a second end, and a width between two opposing side edges; a D-ring fixed with the first end of the flexible band and adapted to receive the second end therethrough, the flexible band having a two-part mechanical fastener having a first-part thereof fixed proximate the first end of the flexible band, and a second part of the two-part mechanical fastener being fixed with the flexible band adjacent the first part of the two-part mechanical fastener;

encapsulating a portion of the flexible band in a silicon rubber material;

providing a toric ring fixed with the flexible band proximate the D-ring, the D-ring being disposed between the toric ring and the first end of the flexible band;

wherein the toric ring includes an open mesh having two opposing ends, a central ring fixed with each of the two opposing ends and having a central area, a central nodule fixed within the central area and with the open mesh, the central nodule comprising a top side with a permanently concave actuator and a bottom side with a complex convex surface, the open mesh being located between the permanently concave actuator and the complex convex surface of the central nodule; and whereby when the epicondylitis brace assembly is fixed about the person's elbow, the complex convex surface contacts either the person's medial epicondyle or the person's lateral epicondyle so that pressure is applied to either the medial epicondyle or a lateral epicondyle by a force of the open mesh, and additional pressure applied to the permanently concave actuator serves to cause the complex convex surface to apply pressure to either the medial epicondyle or the lateral epicondyle.

* * * * *